United States Patent
Byun et al.

(10) Patent No.: US 6,764,698 B1
(45) Date of Patent: Jul. 20, 2004

(54) CONTROLLED DRUG RELEASE SYSTEM OF RETINOIC ACID

(75) Inventors: Young-Ro Byun, Kwangju (KR); Sang-Yoon Kim, Seoul (KR); Sun-Hee Kim, Seoul (KR); Yong-Doo Choi, Kwangju (KR); In-Suk Han, Salt Lake City, UT (US); Kwang-Sun Lee, Seoul (KR); Chul-Hee Kim, Sungnam-shi (KR)

(73) Assignees: Kwangju Institute of Science & Technology, Kwangju (KR); Shin Poong Pharmaceutical Co., Ltd., Kyunggi-do (KR)

( * ) Notice: Subject to any disclaimer, the term of this patent is extended or adjusted under 35 U.S.C. 154(b) by 0 days.

(21) Appl. No.: 09/806,287
(22) PCT Filed: Sep. 29, 1999
(86) PCT No.: PCT/KR99/00589
§ 371 (c)(1),
(2), (4) Date: Mar. 28, 2001
(87) PCT Pub. No.: WO00/19996
PCT Pub. Date: Apr. 13, 2000

(30) Foreign Application Priority Data

Oct. 1, 1998 (KR) ......................................... 1998/41426

(51) Int. Cl.[7] ............................ A61K 9/14; A61K 9/16
(52) U.S. Cl. ....................... 424/489; 424/490; 424/491; 424/497; 424/501; 424/426
(58) Field of Search ................................ 424/426, 489, 424/490, 491, 497, 501; 257/4, 4.1, 4.33, 4.6; 514/963, 725

(56) References Cited

U.S. PATENT DOCUMENTS

| | | | | |
|---|---|---|---|---|
| 5,534,261 A | * | 7/1996 | Rodgers et al. | 424/422 |
| 5,543,158 A | * | 8/1996 | Gref et al. | 424/451 |
| 5,665,428 A | * | 9/1997 | Cha et al. | 427/213.3 |

FOREIGN PATENT DOCUMENTS

WO    WO 97/15287    *    5/1997

OTHER PUBLICATIONS

Lippman et al 13–cis–Retinoic Acid Plus Interferon–alpha: Highly Active Systemic Therapy for Squamous Cell Carcinoma of the Cervix J. National Cancer Institute 84(4):241–245 1992.*

* cited by examiner

Primary Examiner—Thurman K. Page
Assistant Examiner—Rachel M. Bennett
(74) Attorney, Agent, or Firm—Peter F. Corless; John B. Alexander; Edwards & Angell, LLP (57) ABSTRACT

The present invention relates to a controlled drug release system in which a certain ratio or retinoic acid is incorporated into a microsphere comprising biodegradable polymer and amphoteric block copolymer having both hydrophilic and hydrophobic groups.

5 Claims, 11 Drawing Sheets

Fig.6b

CONTROLLED DRUG RELEASE SYSTEM OF RETINOIC ACID

TECHNICAL FIELD

The present invention relates to a controlled drug release system in which a certain ratio of retinoic acid (herein after referred to as "RA") is incorporated into a microsphere comprising biodegradable polymer and amphiphilic copolymer having both hydrophilic and hydrophobic groups.

BACKGROUND ART

Retinoic acid has been known to have roles in controlling the differentiation and growth of cells and reportedly inhibits carcinogenesis in various epithelial tissues. It has especially been known to have good effects on the prevention and treatment of cancers such as head and neck cancer, skin cancer, lung cancer, breast cancer, cervical cancer, bladder cancer, etc. and also exhibits efficacy in patients suffering from acute promyelocytic leukemia [See, Blood 76, 1704–1709 (1990), Blood 78, 1413–1419 (1991); and, The New England Journal of Medicine 324, 1385–1393 (1991)].

However, upon continuous repetitive administration of retinoic acid, drug level in blood is rapidly decreased compared with the early stage of treatment [Blood 79, 299–303 (1992)], and the diseases are recurred within a short period [Cancer Research 52, 2138–2142 (1992)]. This is because the oral administration of retinoic acid induces cytochrome P450 enzyme which metabolizes retinoic acid. Even in a case where a small amount of retinoic acid is administered, cytochrome P450 is induced, and repeated administration would accelerate the metabolism by the enzyme and thus it is impossible to maintain effective retinoic acid level in blood. If the level of retinoic acid increases, severe side toxic effects would appear, and even result in difficulty in breathing, spasm, comatose state which leads to death. In order to solve these problems, drug release systems for retinoic acid using liposome [Leukemia Research 18, 587–596 (1994)] or nanoparticle [International Journal of Pharmaceutics 131, 191–200 (1996)] have been tried, but these systems have a drawback that the control of drug release is difficult.

As another prior art reference for delayed retinoic acid release system, it has been reported that retinoic acid was released over 40 days by incorporating retinoic acid into a microsphere prepared from lactic acid and poly(lactic-co-glycolic acid), (hereinafter referred to as "PLGA") [see, investigative Ophthalmology & Visual Science 34, 2743–3751 (1993)]. The system was focused on the treatment of proliferative vitreoretinopathy. However, the microsphere prepared by this technique has a drawback that it is difficult to be dispersed into an aqueous phase. In addition, since ethylene oxide is impossible for applying gas sterilization, gamma-ray sterilization should be used. Even if, such gamma-ray sterilization is carried out on the microsphere, the molecular weight thereof is decreased. Further, this prior art system fails to teach the use of amphiphilic copolymer in controlling the dissolution rate of the microsphere and the release rate of retinoic acid.

DISCLOSURE OF INVENTION

It is therefore an object of the present invention to solve the problems associated with the prior art release system.

Another object of the present invention is to provide a controlled drug release system for retinoic acid which comprises microsphere in which the biodegradable polymer and amphiphilic block copolymer and retinoic acid incorporated into the microsphere.

Further objects and advantages of the invention will become apparent through reading the remainder of the specification.

The foregoing has outlined some of the more pertinent objects of the present invention. These objects should be construed to be merely illustrative of some of the more pertinent features of the invention. Many other beneficial results can be obtained by applying the disclosed invention in a different manner or by modifying the invention within the scope of the disclosure. Accordingly, other objects and a more thorough understanding of the invention may be found by referring to the detailed description of the preferred embodiment in addition to the scope of the invention defined by the claims.

BRIEF DESCRIPTION OF DRAWINGS

FIG. 1 is a photograph showing the morphology of microsphere according to the contents of poly-L-lactic acid-polyethyleneglycol block copolymer:
  (a)-without DiPLE; (b)-with 4% of DiPLE; (c)-with 8 wt % of DiPLE; and (d)-with 10 wt % of DiPLE.

FIG. 2 represents a graph in which the surface compositions of the microspheres were analysed with X-ray photoelectric spectrum:
  (a)-microsphere containing 8% of DiPLE; (b)-microsphere containing 4% of DiPLE; and (c)-surface composition of DiPLE test sample.

FIG. 3 is a photograph showing the morphology of poly-D,L-lactic acid microsphere according to the mixing ratio of TriPLE: (a)-5 wt % of TriPLE 2-1; (b)-15 wt % of TriPLE 2-1; (c)-100 wt % of TriPLE 2-1; (d)-5 wt % of TriPLE 3-1; (e)-20 Wt % of TriPLE 3-1; and (f)-100 wt % of TriPLE 3-1.

FIG. 4 is a photograph showing the morphology of poly-L-lactic acid microsphere according to the content of retinoic acid (RA);
  (a) microsphere size: 1~10 μm, RA content: 4 wt %;
  (b) microsphere size: 1~10 μm, RA content: 8 wt %;
  (c) microsphere size 20~100 μm, RA content: 4 wt %;
  (d) TriPLE 2-1 microsphere size 20~100 μm, RA content: 5 wt %; and
  (e) TriPLE 2-1 microsphere size 20~100 μm, RA content: 10 wt %.

FIG. 5 is a graph showing drug release curves according to DiPLE and RA content within the microsphere, in which
  (a) represents the curve when RA is 2 wt %, and DiPLE varies at 0 wt %, 4 wt %, and 8 wt %;
  (b) represents the curve when RA is 4 wt %, and DiPLE varies at 0 wt %, 4 wt %, 8 wt %; and
  (c) represents the curve when RA is 8 wt %, and DiPLE varies at 4 wt %, 8 wt %.

FIG. 6 is a photograph showing inhibition of tumour growth by the drug release system according to the invention, in which
  (a) represents the control tumour-induced mouse at five weeks after administering a release system which does not contain retinoic acid; and
  (b) represents the test mouse at five weeks after administering the release system according to the invention which contains retinoic acid(DiPLE 8 wt %, RA 4 wt %).

BEST MODE FOR CARRYING OUT THE INVENTION

Hereinafter, the invention will be illustrated in more detail.

The present inventors have conducted an extensive research for many years in order to develop a new drug release system in which the prior art drawbacks are eliminated. As a result, the inventors have surprisingly discovered that when retinoic acid is incorporated into a microsphere prepared from biodegradable polymer such as PLLA, PDLLA, or PLGA and amphoteric poly-L-lactic acid-polyethyleneglycol block copolymer("PLE"), retinoic acid is released over long term period in a sustained pattern and thus, this release system can improve the prior art drawbacks, for example can reduce resistance induction by the conventional retinoic acid administration, and can be used in the prevention or treatment of leukemia and various cancers, and have completed the present invention.

In one aspect, the present invention provides a controlled drug release system which comprises a microsphere in which biodegradable polymer and amphiphilic block copolymer are mixed together and retinoic acid incorporated into the microsphere.

Retinoic acid which can be used as the active ingredient in the drug release system according to the present invention has no limitation and include, for example, all-trans-retinoic acid, 13-cis-retinoic acid, 9-cis-retinoic acid, other retinoids and the mixture thereof.

As for the biodegradable polymer used in the preparation of microsphere, any polymeric material can be used without any limitation if it has bioavailable and biodegradable properties as the support for the microsphere. Such polymers include natural and synthetic origins, and the examples thereof are set forth in Table 1 below.

TABLE 1

Biodegradable polymer

| Polymer | Classification | Specific polymer |
| --- | --- | --- |
| Synthetic polymer | Polyesters | Poly(L-lactic acid), Poly(D,L-lactic acid) Poly(glycolic acid), Poly(lactic-co-glycolic acid), Polyhydroxybutyrate, poly(valerolactone), Poly($\epsilon$-caprolactone) |
| | Polyanhydrides | Poly[bis(p-carboxyphenoxy)propane-cosebacic acid], Poly(fatty acid dimer-co-sebacic acid) |
| | Polyphosphazenes | Aryloxyphosphazene polymer, Amino acid ester system |
| | Poly(ortho esters) | |
| Natural polymer | Polysaccharides | Cellulose, Starch, Chondroitin sulfate |
| | Proteins | Albumin, Collagen |

The above polymer can be used either solely or in admixture of two or more individual polymers.

The biodegradable polymer which can be desirably used in the present invention includes poly-L-lactic acid (hereinafter referred to "PLLA"), Poly-D,L-lactic acid (hereinafter referred to as "PDLLA"), and poly lactic-co-glycolic acid (hereinafter referred to as "PLGA").

The biodegradable polymer is mixed with a suitable amount of a polymeric surfactant to prepare the microsphere of the invention. This polymeric surfactant is added in order to control the dissolution rate of microsphere and drug release rate.

Any of polymeric surfactants may be preferably used without limitation provided that they are amphiphilic block copolymers having hydrophilic and hydrophobic groups, the example of which includes di-, tri- or multi-block copolymer or graft copolymer of the biodegradable polymer as mentioned in the above and polyethylene glycol. As such surfactant, polylactic acid-polyethylene glycol block copolymer is preferred, with poly-L-lactic acid-polyethyleneglycol di-block copolymer (PLLA-PEG, hereinafter, referred to as "DiPLE") or poly-L-lactic acid-polyethyleneglycol-poly-L-lactic acid tri-block copolymer (PLLA-PEG-PLLA, hereinafter, referred to as "TriPLE") being most preferred.

It is obvious to those skilled in the relevant art that the mixing ratio of the above biodegradable polymer and the amphiphilic polymer within the microsphere can be suitable determined according to the desired effects such as for example release pattern of retinoic acid. However, it is desirable that the ratio be selected within the range of 1:0~100 part by weight based on the biodegradable polymer.

The suitable particle size of the microsphere is within the range from 0.001~1000 $\mu$m, preferably from 1 to 100 $\mu$m.

Meanwhile, the mixing ratio of retinoic acid and microsphere is preferably within the range between 0.1~50 wt % based on the weight of microsphere.

EXAMPLES

The present invention will be described in greater detail through the following examples. The examples are presented for illustrating purposes only and should not be construed as limiting the invention which is properly delineated in the claims.

Example 1

Synthesis of Polymeric Surfactant 1.1. Synthesis of Poly-L-lactic Acid-polyethyleneglycol Di-block Copolymer Poly-L-lactic acid-polyethylene glycol di-block copolymer used as the polymeric surfactant (DiPLE) was synthesized by ring opening polymerization of L-lactide using mono-methoxy polyethyleneglycol as the initiator. L-lactide was recrystalized twice from ethyl acetate and monomethoxy polyethyleneglycol was used after drying under reduced pressure at 60° C. for 8 hours.

First, 6.507 g of L-lactide, 2 g of monomethoxy polyethyleneglycol(Mn 5,000), and 45 ml of toluene were poured into a three-necked flask equipped with stirrer, nitrogen inlet and reflux condenser and heated at 70° C. until two reactants are completely dissolved into toluene. Continuously, 65 mg of catalyst, stannous octoate was added into the flask and the solvent, toluene was refluxed at 110° C. for 24 hours. After removing the solvent under reduced pressure, the resulting product was dissolved into chloroform, and then purified by precipitating into each of mixed solutions of acetone/diethyl ether(1:4 v/v) and methanol/hexanol(4:1 v/v) to give the poly-L-lactic acid-polyethylene glycol di-block copolymer.

1.2: Synthesis of Poly-L-lactic Acid-polyethylene Glycol Tri-block Copolymer

Poly-L-lactic acid-polyethylene glycol-poly-L-lactic acid (PLLA-PEG-PLLA) tri-block copolymer used as the polymeric surfactant(TriPLE) was synthesized by ring opening polymerization of L-lactide using polyethyleneglycol as the initiator. The initiator, polyethyleneglycol (trademarks designated molecular weight 4600, 2000, 600, Aldrich chemical company, USA) was used after dissolving into chloroform, precipitating into diethyl ether and then drying at vacuum.

The synthesis was carried out in the same manner as in the di-block copolymer (DiPLE) synthesis and the amounts added upon synthesis are shown in Table 2 below.

TABLE 2

The amounts of polyethyleneglycol, L-lactide, and stannous octoate

| Block copolymer | PEG $M_n$ by GPC | PEG (g) | L-lactide (g) | St-oct (mg) |
|---|---|---|---|---|
| TriPLE 1-1 | 5,200 | 2.00 | 7.84 | 78 |
| TriPLE 1-2 | | 2.00 | 12.20 | 12 |
| TriPLE 1-3 | | 1.00 | 8.25 | 82 |
| TriPLE 2-1 | 2,200 | 1.00 | 9.00 | 90 |
| TriPLE 2-2 | | 0.60 | 9.38 | 94 |
| TriPLE 2-3 | | 0.50 | 9.50 | 95 |
| TriPLE 3-1 | 616 | 0.30 | 9.00 | 90 |
| TriPLE 3-2 | | 0.203 | 9.314 | 93 |
| TriPLE 3-3 | | 0.153 | 9.504 | 95 |

The result of analysis on the final product of poly-L-lactic acid-polyethylene glycol block copolymer is as follows:

$^1$H-NMR (400 MHz, chloroform(CDCl$_3$)): δ 1.58 (—CH$_3$ of PLLA), 5.19 (—CH of PLLA), 3.65 (—O—CH$_2$—CH$_2$ of PEG).

FT-IR: 1758 cm$^{-1}$ (CO), 1300–1000 cm$^{-1}$ (COO), 2882 cm$^{-1}$ (CH$_2$).

In addition, the molecular weight and thermal characterization of the synthesized polymer measured by gas permeation chromatograph, etc. were represented in Table 3.

TABLE 3

The molecular weight and thermal characterization of the synthesized polymer

| Block copolymer | Chemical structure | $M_n$[1] | MWD[1] | $T_g$ (° C.)[2] | $T_m$ (° C.)[2] |
|---|---|---|---|---|---|
| DiPLE | EG$_{113}$-LA$_{191}$ | 32,500 | 1.46 | 18~40 | 169 |
| TriPLE 1-1 | LA$_{145}$-EG$_{118}$-LA$_{145}$ | 26,000 | 1.23 | 51.2 | 167 |
| TriPLE 1-2 | LA$_{223}$-EG$_{118}$-LA$_{223}$ | 38,700 | 1.21 | 51.8 | 173.5 |
| TriPLE 1-3 | LA$_{275}$-EG$_{118}$-LA$_{275}$ | 44,800 | 1.19 | 52.6 | 175.4 |
| TriPLE 2-1 | LA$_{142}$-EG$_{50}$-LA$_{142}$ | 22,600 | 1.48 | 55.1 | 175.1 |
| TriPLE 2-2 | LA$_{217}$-EG$_{50}$-LA$_{217}$ | 33,500 | 1.30 | 55.8 | 178.1 |
| TriPLE 2-3 | LA$_{312}$-EG$_{50}$-LA$_{312}$ | 47,100 | 1.31 | 56.3 | 175.4 |
| TriPLE 3-1 | LA$_{140}$-EG$_{14}$-LA$_{140}$ | 20,800 | 1.23 | 50.2 | 169.5 |
| TriPLE 3-2 | LA$_{233}$-EG$_{14}$-LA$_{233}$ | 34,200 | 1.22 | 52.7 | 172.9 |
| TriPLE 3-3 | LA$_{340}$-EG$_{14}$-LA$_{340}$ | 49,500 | 1.21 | 53.9 | 173.1 |

[1]determined by GPC (gel permeation chromatography)
[2]determined by DSC (differential scanning calorimetry)

Example 2

Preparation of Microsphere with Poly-L-lactic Acid-polyethylene Glycol Di-block Copolymer (DiPLE)

Microsphere was prepared from poly-L-lactic acid (PLLA) and poly-L-lactic acid-polyethylene glycol di-block copolymer (DiPLE) by the oil-in-water (O/W) emulsion solvent evaporation method which is conventionally used in the hydrophobic drug manufacture.

In order to determine the optimum content of polymeric surfactant, DiPLE obtained in Example 1 within microsphere, the morphology of microsphere was observed according to the mixing ratios of DiPLE.

First, 250 mg of poly-L-lactic acid and DiPLE(0, 2, 4, 6, 8, 10, 20 and 30 wt %) were dissolved into 5 ml of dichloromethane, and then subjected to homogenization at 24,000 rpm for 10 minutes with a homogenizer under vigorous stirring while injecting 40 ml of aqueous 2 w/v % polyvinyl alcohol solution with a needle gauge thereinto. Dichloromethane was evaporated for 2 hours at 40° C. The microsphere formed by poly-L-lactic acid coagulation was washed three times with distilled water to remove polyvinyl alcohol, collected by centrifugation and then freeze-dried for 24 hours.

Example 3

Preparation of Microsphere with Poly-D,L-lactic Acid-polyethylene Glycol Tri-block Copolymer (TriPLE)

Microsphere was prepared by the oil-in-water (O/W) emulsion solvent evaporation method. 200 mg of poly-D, L-lactic acid and the synthesized TriPLE(0, 5, 10, 15, 20, and 100 wt %) were dissolved into 5 ml of dichloromethane, and the organic solution was vigorously stirred(rpm 1,000) with a mechanical stirrer while pouring it into 200 ml of aqueous 2 w/v % polyvinyl alcohol solution. The subsequent procedures were followed by Example 2.

Example 4

Inclusion of Retinoic Acid

The work for incorporating retinoic acid into the microsphere was carried out in a dark room in order to prevent retinoic acid from decomposition by light.

4.1 Preparation of Poly-L-lactic Acid Microsphere with DiPLE

Two types of microspheres were prepared having particle size of 1~10 μm and 20~100 μm, respectively.

In order to prepare the microsphere having particle size of 1~10 μm, 250 mg of poly-L-lactic acid and DiPLE(0, 4, and 8 wt %) and retinoic acid (2, 4, and 8 wt %) were first dissolved into 5 ml of dichloromethane, and then subjected to homogenization at 24,000 rpm for 10 minutes with a homogenizer under vigorous stirring while injecting 40 ml of aqueous 2 w/v % polyvinyl alcohol solution with a needle gauge thereinto. The remaining procedures are the same as in Example 2.

In order to prepare the microsphere having particle size of 20~100 μm, 3.75 g of poly-D,L-lactic acid, DiPLE (8 w %) and retinoic acid (4 wt %) were dissolved into 75 ml of dichloromethane, and the organic solution was vigorously stirred(rpm 1,000) with a mechanical stirrer while pouring it into 600 ml of aqueous 2 w/v % polyvinyl alcohol solution. The remaining procedures are the same as in Example 2.

4.2: Preparation of Poly-D,L-lactic Acid Microsphere with DiPLE

Microsphere was prepared by the oil-in-water (O/W) emulsion solvent evaporation method. First, 400 mg of poly-D,L-lactic acid (Molecular weight: 17,500), DiPLE(0 or 8 wt %) and retinoic acid (10 wt %) were dissolved into 10 ml of dichloromethane, and the organic solution was stirred(rpm 1,000) with a mechanical stirrer while pouring it into 200 ml of aqueous 2 w/v % polyvinyl alcohol solution. The remaining procedures are the same as in Example 2.

4.3: Preparation of Microsphere with TriPLE

Microsphere was prepared by the O/W emulsion solvent evaporation method. 600 mg of TriPLE and retinoic acid (0, 5, or 10 wt %) were dissolved into 15 ml of dichloromethane, and the organic solution was stirred(rpm 1,000) with a mechanical stirrer while pouring it into 200 ml of aqueous 2 w/v % polyvinyl alcohol solution. The remaining procedures are the same as in Example 2.

Experiment 1

Characterization of Microsphere

The morphology of the microspheres obtained in Examples 2 and 3 was observed with scanning electron microscope(SEM). In order to investigate the dispersibility in the dispersed solution, the degree of dispersion of microspheres was evaluated in phosphate buffer solution of pH 7.4, and 1(ionic strength) 0.15.

1.1. Poly-L-lactic Acid Microsphere with DiPLE

Figure 1A:
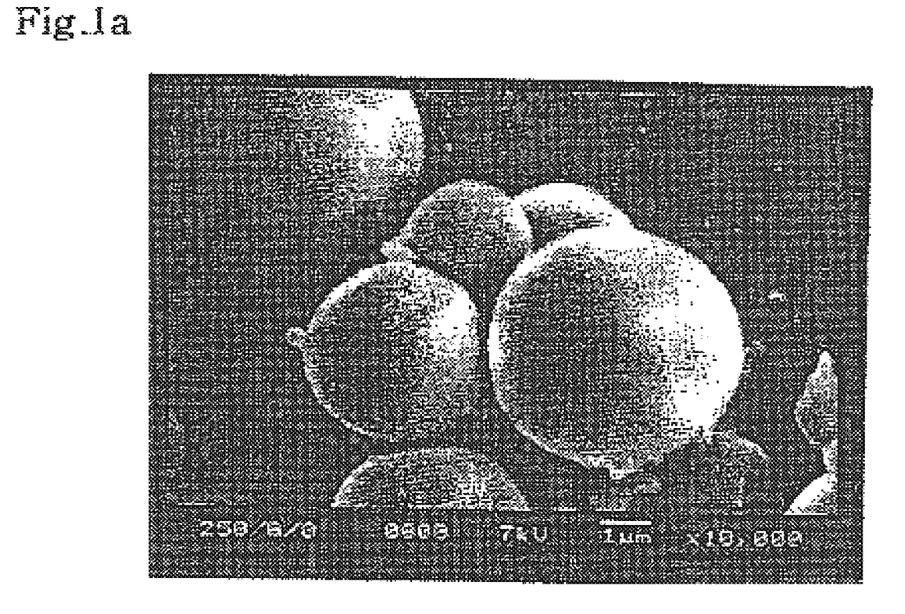
Figure 1B:
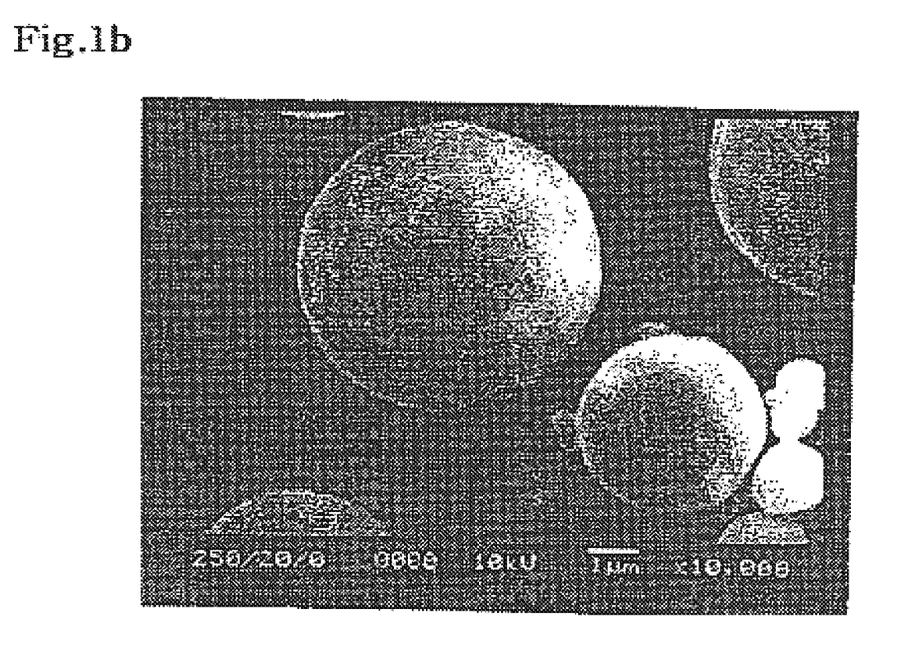
Figure 1C:
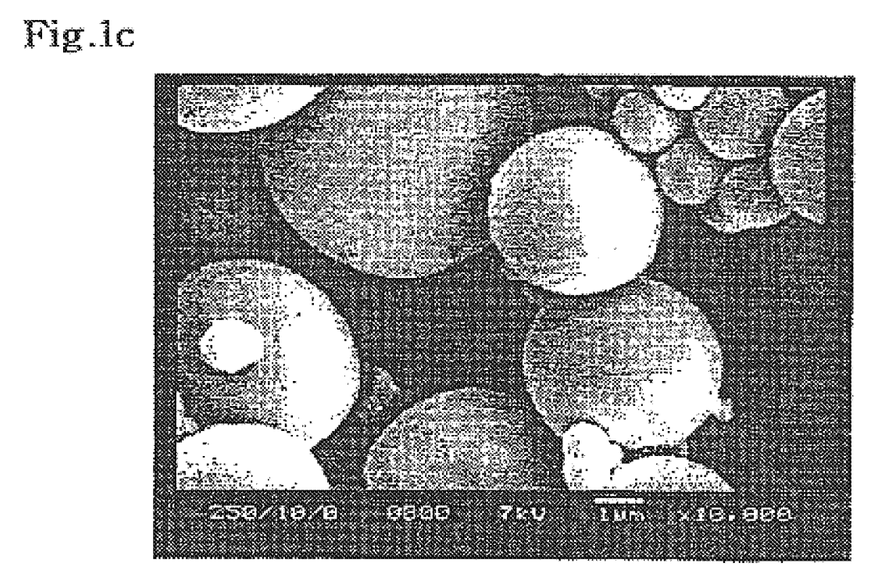
Figure 1D:
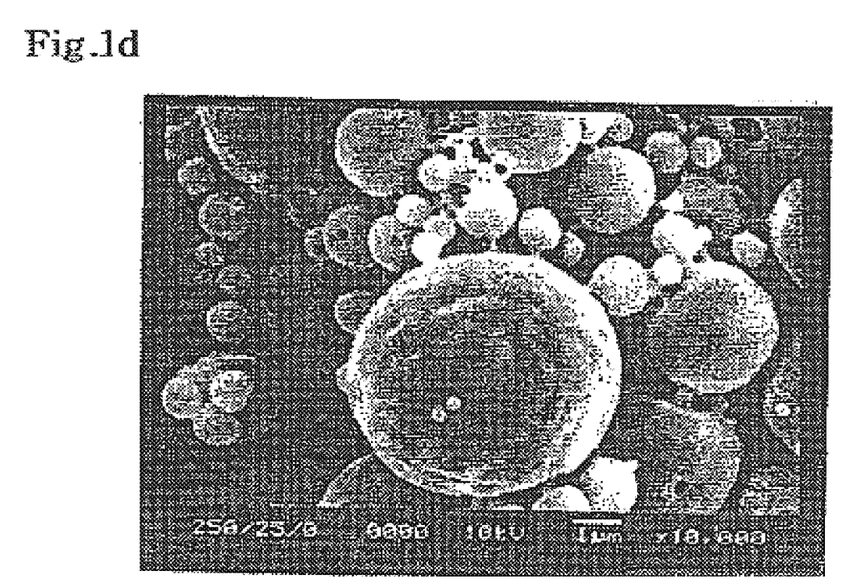

The morphology of microsphere according to the content of DiPLE is shown in FIG. 1(a), (b), (c) and (d). As the content of DiPLE increases, the surface of microsphere became irregular. Microsphere having smooth surface was obtained at the content of up to 8 wt % of DiPLE.

In the dispersibility test within PBS, the microsphere containing 2% or more of PLE was well dispersed, even without addition of the surfactant such as Tween 20 into the aqueous solution. Dispersibility was increased as the content of PLE increases.

Figure 2A:
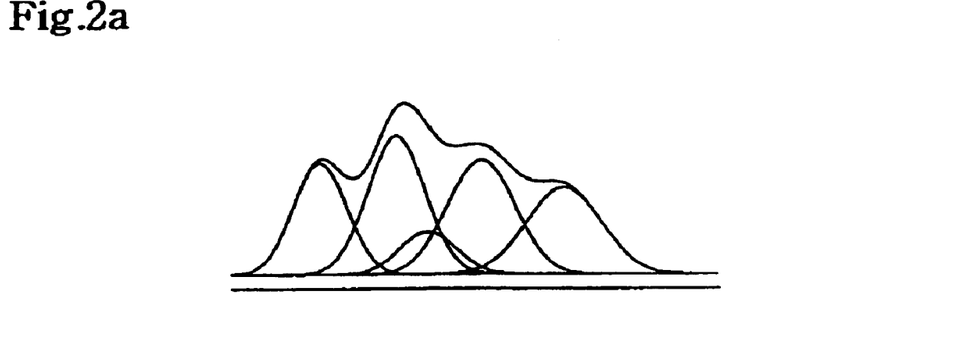
Figure 2B:
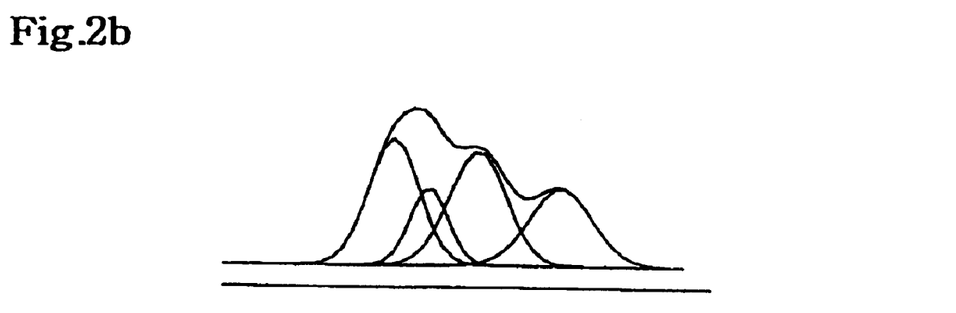
Figure 2C:
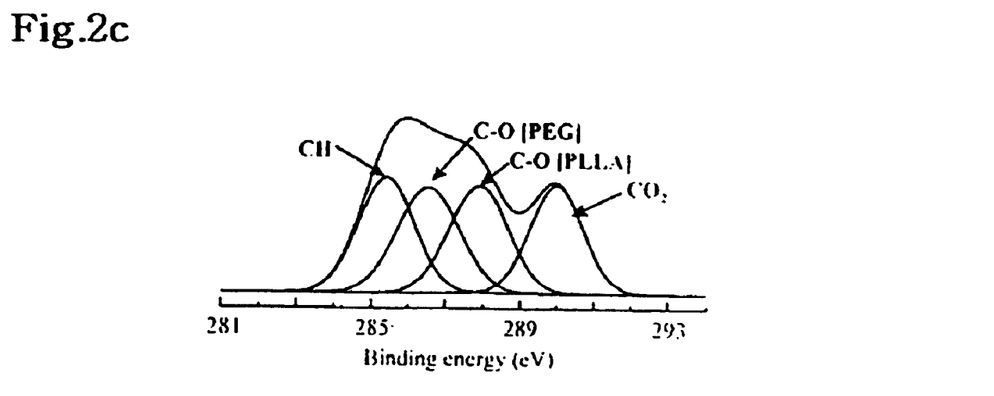

The composition within the microsphere surface was analyzed by X-ray photoelectric spectrophotometry as shown in FIG. 2. The peaks at 285.5 eV, 287.5 eV and 289.6 eV correspond to the binding energy of —CH—, —CO— and —$CO_2$— of PLLA, respectively and the peak at 286.55 eV corresponds to C—C—O— of polyethylene glycol.

As can be seen from FIG. 2, the relative strength of the peak at 286.55 eV due to PEG chain was increased as the content of PLE within the microsphere increases. This suggests that as the content of DiPLE increases, die density of PEG chain on the microsphere surface increases. This is because dispersibility in PBS solution increases as the content of PLE increase.

As a result of SEM observation and the dispersion experiment within PBS, it was confirmed that the suitable DiPLE content for preparing microsphere according to the invention is within the range of 2~8 wt %.

1.2. Poly-D,L-lactic Acid Microsphere with TriPLE

The prepared microspheres showed diverse surface morphology according to the kinds of TriPLE and the mixing ratios thereof as shown in FIG. 3 and the differences in size was not observed in the microspheres. Generally, as the mixing ratio of TriPLE increases, the surface of microsphere became a wrinkled shape and when the mixing ratio is 100%, microspheres in irregular shape were obtained (FIG. 3a~c)).

Figure 3A:
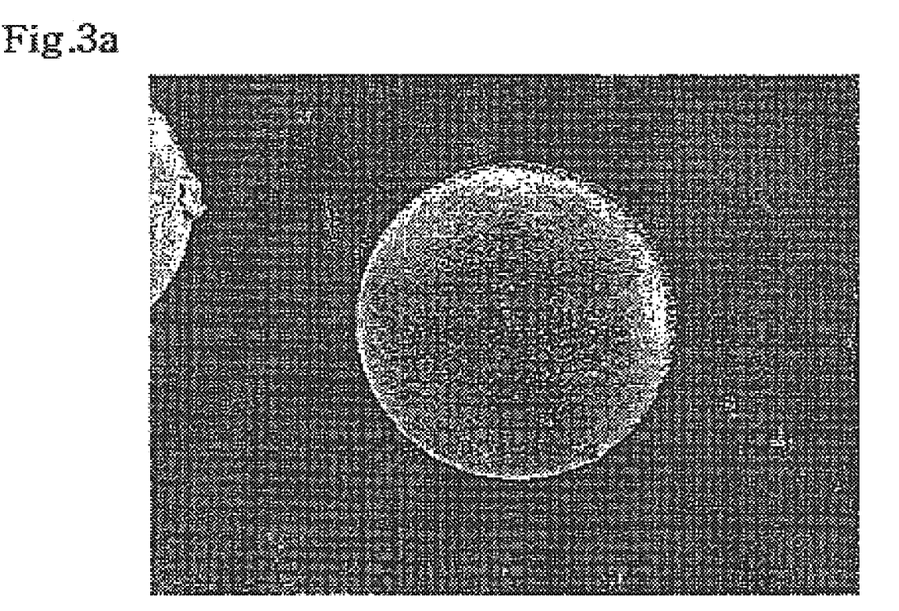
Figure 3B:
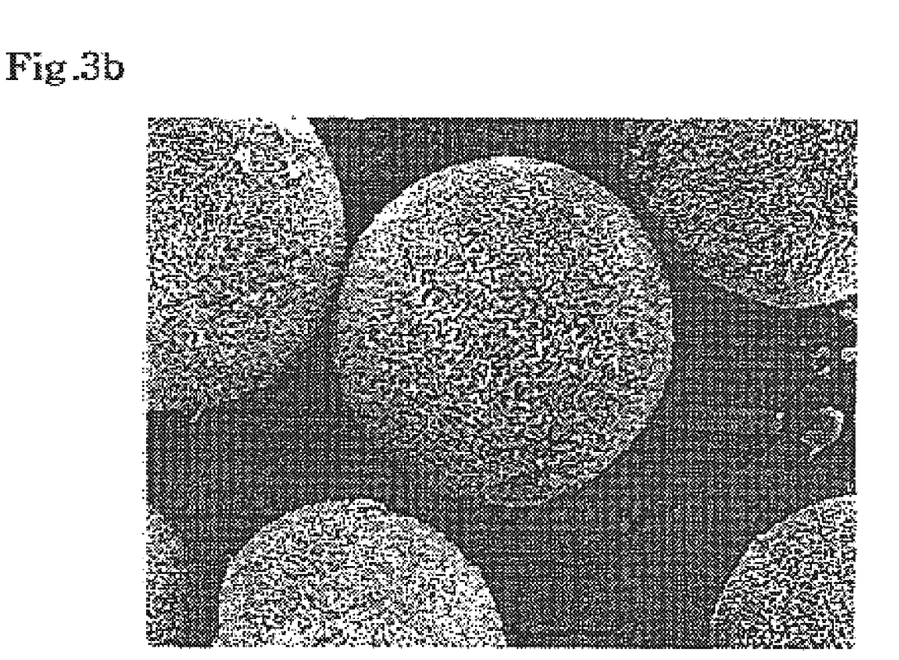
Figure 3C:
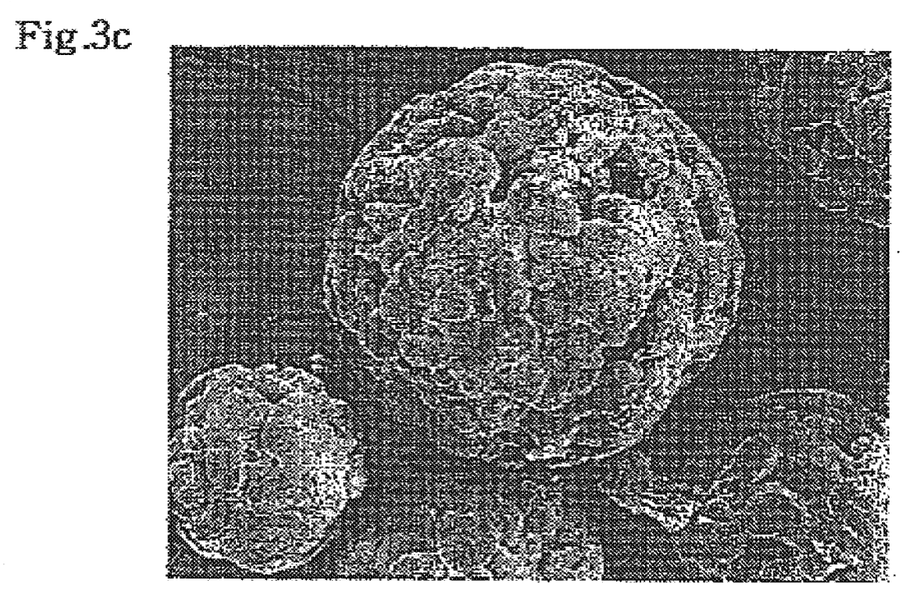
Figure 3D:
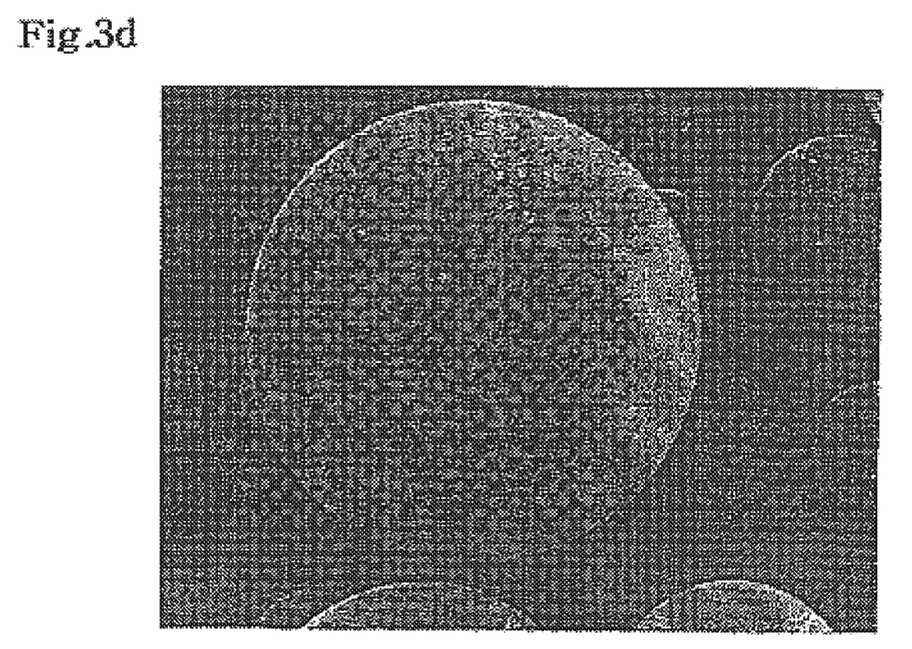
Figure 3E:
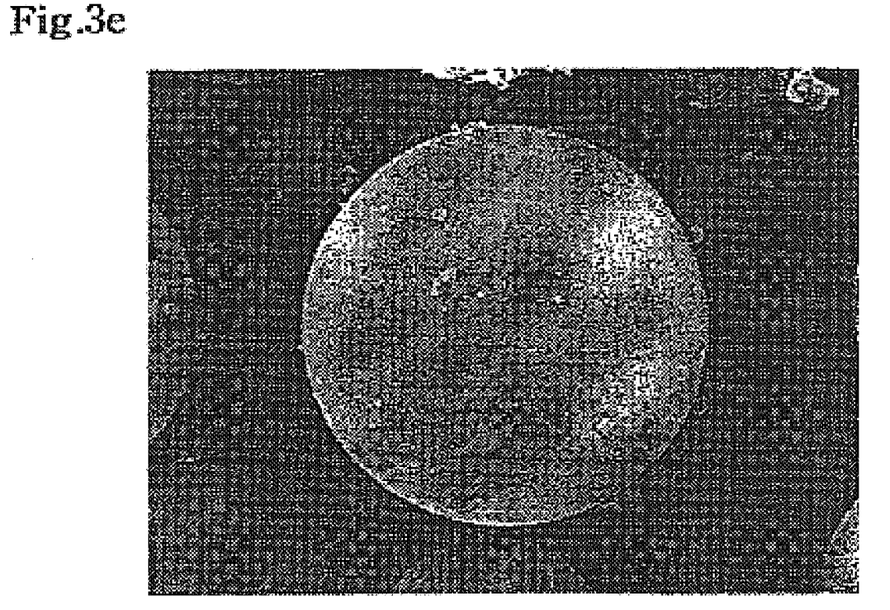
Figure 3F:
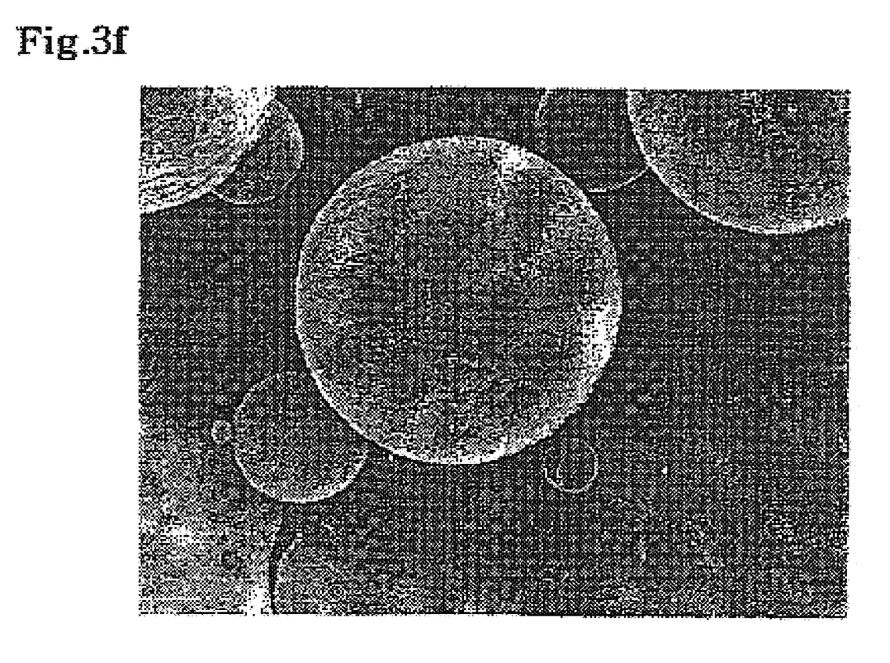

In addition, if the ratio of central polyethylene glycol blocks to the poly-L-lactic acid blocks in both ends increases, the surface wrinkles were increased (FIG. 3(b) and (e)).

In the microspheres that the third group of TriPLE is mixed, smooth surface of microsphere was observed as in the microsphere prepared with poly-D,L-lactic acid only, even if the mixing ratio was up to 20 wt %.

Experiment 2

Figure 4A:
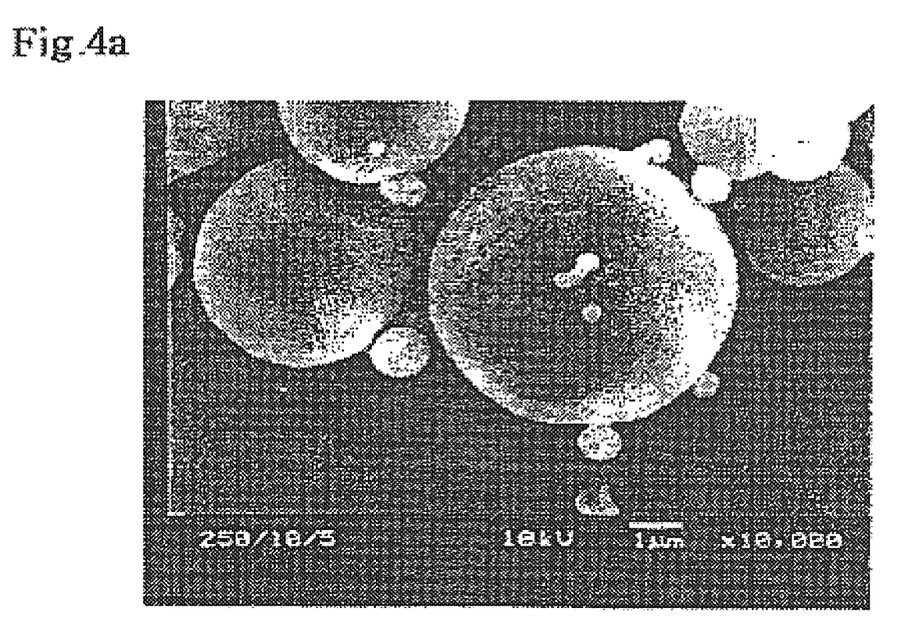
Figure 4B:
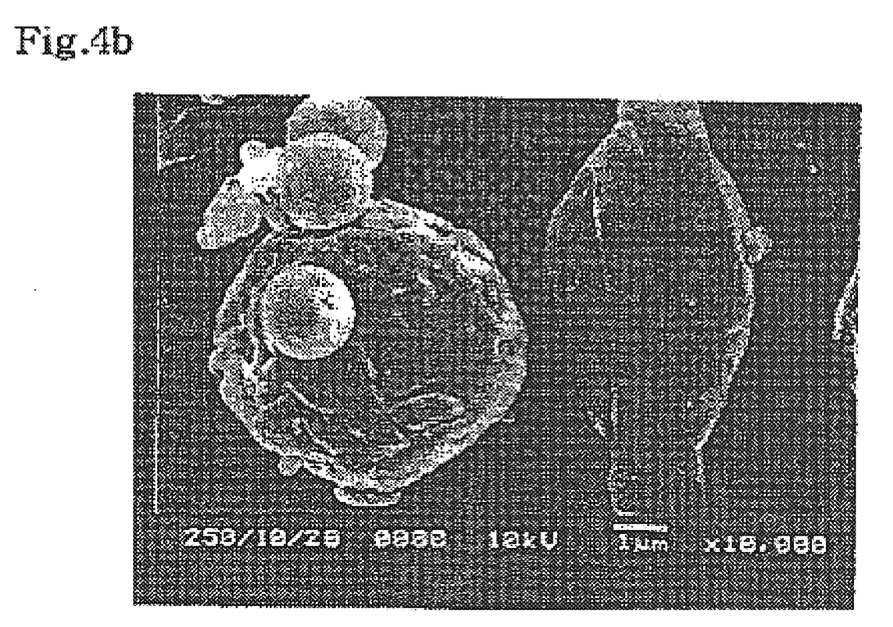
Figure 4C:
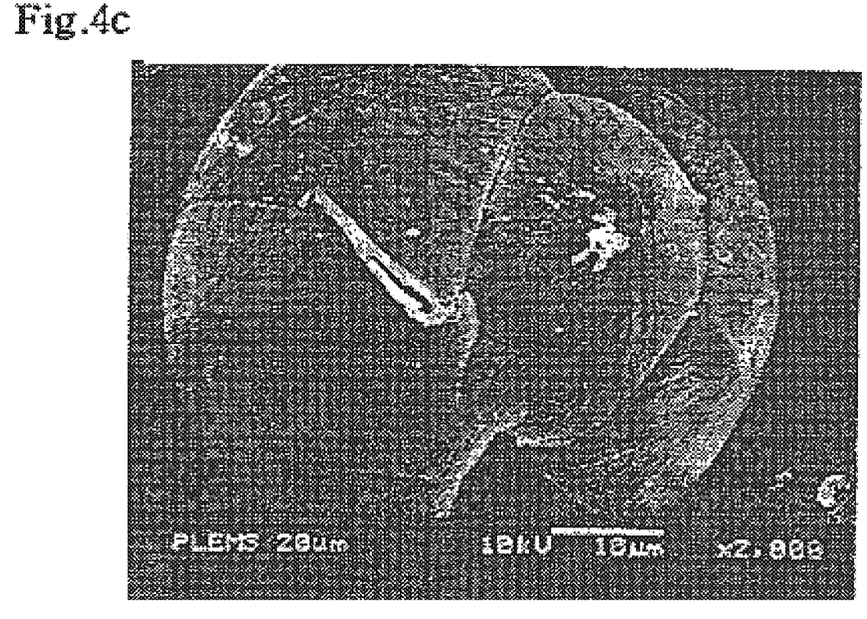

Analysis of Microsphere Based on Particle Size and Content of Retinoic Acid 2.1. Poly-L-lactic Acid Microsphere with DiPLE The morphology of microsphere according to the changes in the content of retinoic acid was observed with SEM and the results are shown in FIG. 4(a)~(c). When the size of microsphere is 1~10 μm, microsphere maintained overall rounded shape as can be seen from FIG. 4(a) to the extent that the content of retinoic acid was up to 4 wt %. However, partially irregular shapes were observed in the microsphere containing 8 wt % of retinoic acid (See, FIG. 4(b)).

When the size is 20~100 μm, as can be seen from FIG. 4(c), microspheres the surface of which is rough and bold-wrinkled lines were formed even if the content of retinoic acid is 4 wt %.

2.2. Microsphere Prepared with TriPLE

Figure 4D:
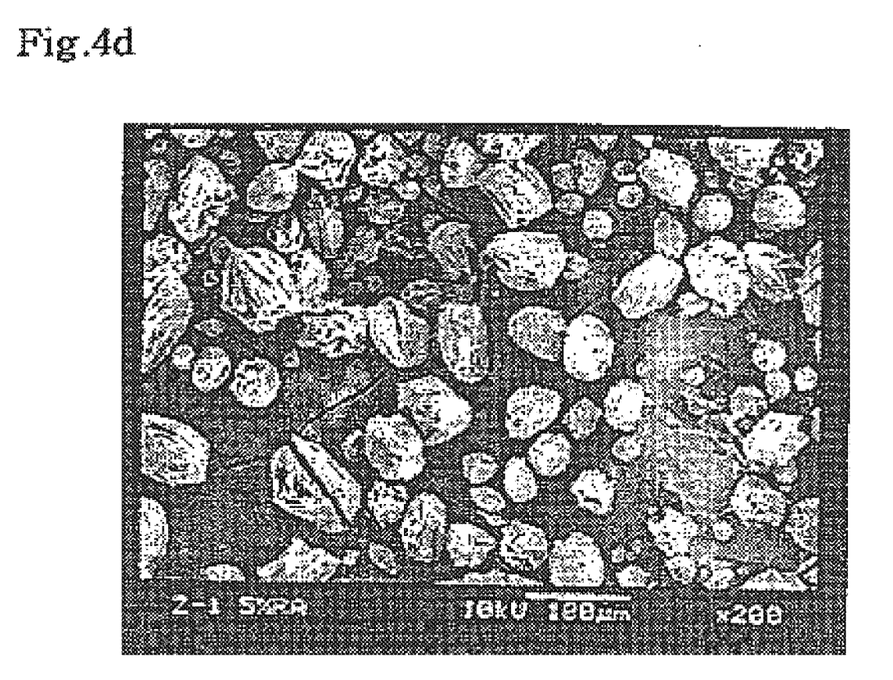
Figure 4E:
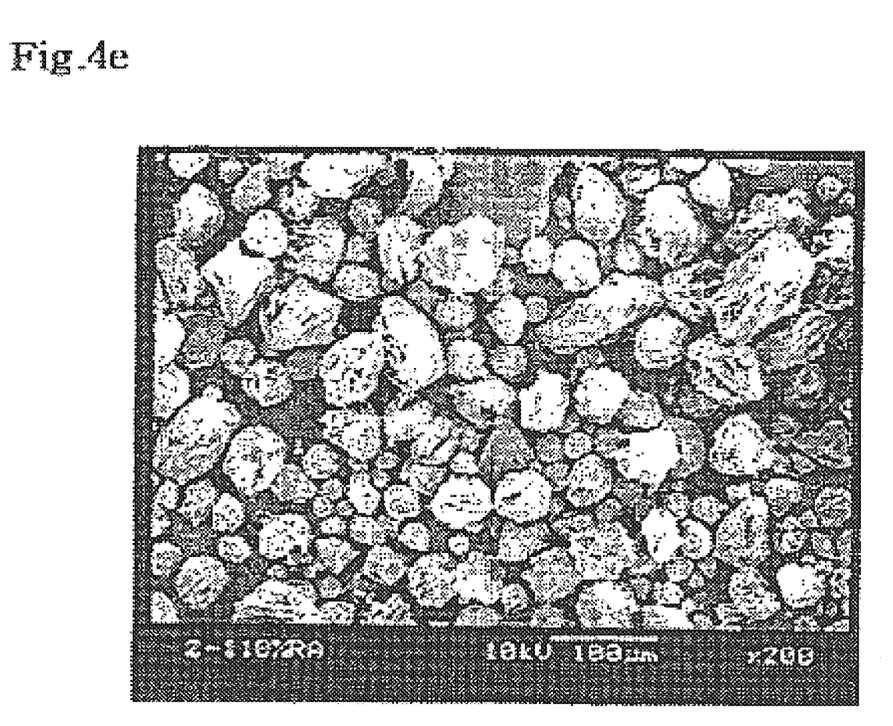

FIG. 4(d)~(e) is a SEM photograph of microsphere prepared from TriPLE 2-1 and retinoic acid (5 and 10 wt %). When prepared from TriPLE only, round, but irregular shaped microsphere was formed. If the drug is contained in the microsphere, this irregularity also increases, and thus, the increase in drug content changed the rounded shape into wrinkled shape.

2.3. Determination of Retinoic Acid Content in Microsphere

The inclusion ratio of retinoic acid into microsphere was determined by measuring ultraviolet(UV) absorbance at 365 nm and comparing the values with calibration curve after dissolving the drug containing microsphere into dichloromethane. The inclusion ratio of retinoic acid was not significantly changed according to the content of PLE or retinoic acid and the inclusion ratio was 90% or more in all cases.

Experiment 3

Release Experiment of Retinoic Acid

Drug release experiment was conducted for the poly-L-lactic acid microsphere in which DiPLE and retinoic acid are mixed as follows:

First, after 10 mg of microsphere containing retinoic acid and 0.5 ml of PBS were added into 1.5 ml microtube, the solution was completely dispersed. The dispersed solution was then put into 6×1.6 cm cellulose acetate membrane and each end of the membrane was sealed. Then, the membrane was immersed in water bath containing 36 l of PBS and stirred at 20 rpm. PBS within the water bath was exchanged at days 9 and 30.

At each measuring period, residual amount of retinoic acid within the microsphere was measured with UV light after membrane was taken from the water bath, washed, dried, and dissolved into dichloromethane. The overall procedures were conducted in a dark room considering the nature of retinoic acid which is sensitive to light.

Figure 5A:
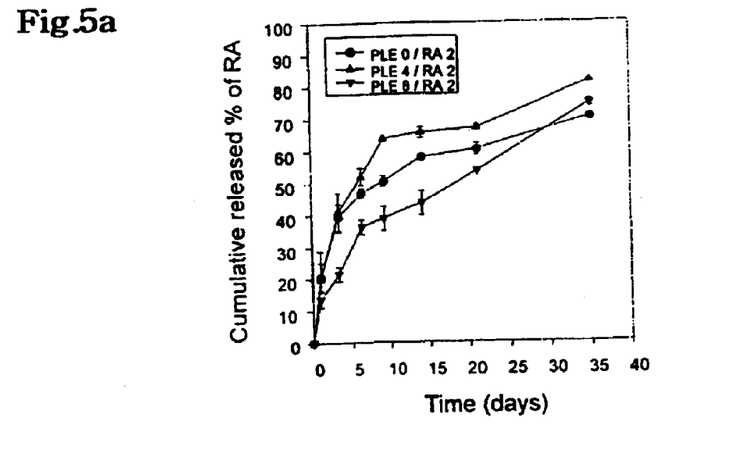
Figure 5B:
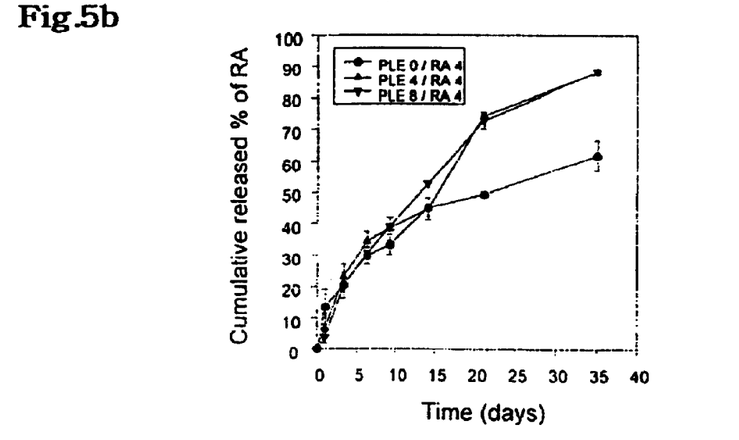
Figure 5C:
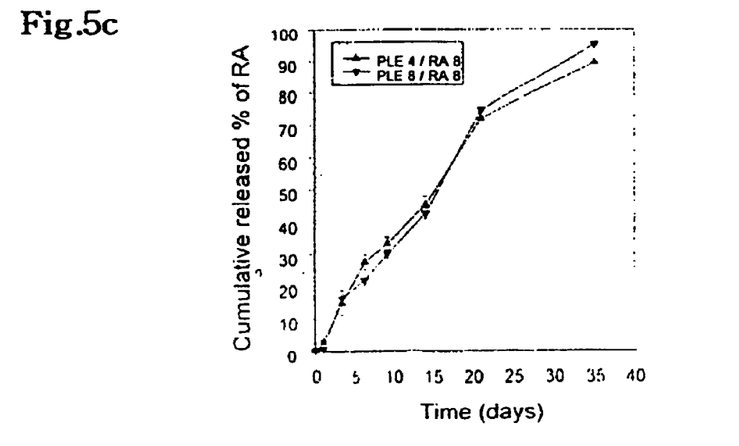

The results on drug release test for the poly-L-lactic acid microsphere prepared by changing the contents of DiPLE and retinoic acid are shown in FIG. 5(a)(b)(c). As can be seen from FIG. 5(a)(b)(c), it was confirmed that retinoic acid in the microsphere according to the invention was released over 35 days and the release rate of retinoic acid from the microsphere was controlled according to the contents of DiPLE and retinoic acid. Especially, in the microsphere containing each 4 wt % of DiPLE and retinoic acid, the drug release curve showed the release pattern similar to zero order drug release which reveals a nearly constant mode in drug release rate.

Experiment 4

Animal Test

Figure 6A:
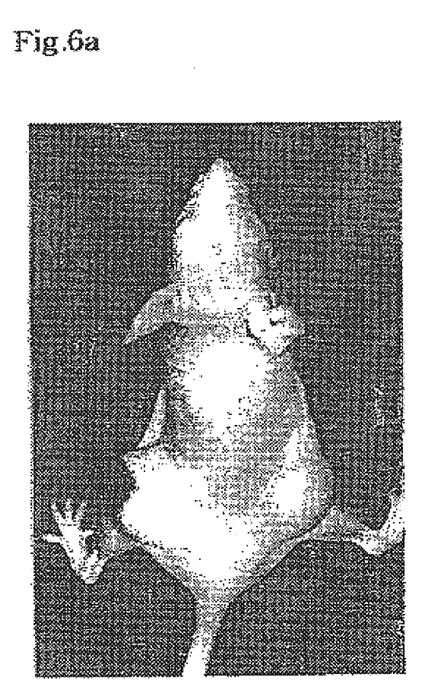
Figure 6B:
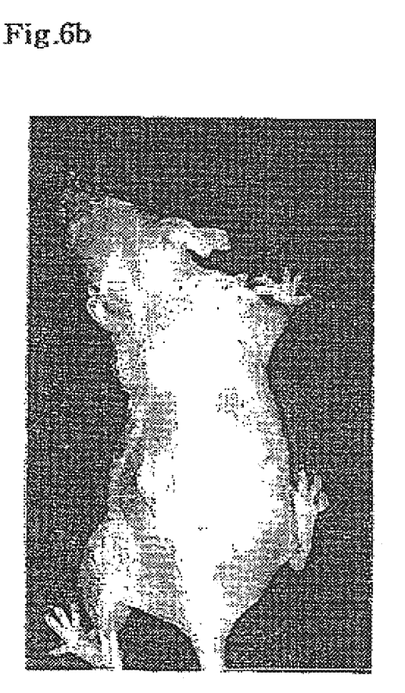

In order to investigate the inhibitory effect against tumour growth by administration of the microsphere containing retinoic acid into mice, 2×10$^6$ cell/ml of tumour cells taken from the patients having head and neck cancer and incubated were subcutaneously injected into the both back sides of the experimental mice weighing 15~31 g at the age of 1.5~2 months in 0.5 ml unit. Then, the mice were divided into two groups. The first group was administered with the microsphere which does not contain retinoic acid, and the second group was administered with poly-L-lactic acid microsphere containing retinoic acid(DiPLE 8 wt %/RA 4 wt %) in each 100 mg/kg dose, and then the size of tumour was recorded at each one week interval. In the meantime, the microsphere was sterilized with ethylene oxide gas before intraperitoneal injection. Tumour cells and microspheres were injected into mice and the changes in tumour growth after 5 weeks were represented in FIG. 6(a) and (b). Tumour cells were grown up to the average size of 1700 mm$^3$ in the mice inoculated with microsphere without retinoic acid (See, 6(a)). However, tumour cells were grown to 300 mm$^3$ in the mice inoculated with microsphere with retinoic acid (See, 6(b)). This value corresponds to 18% of the control, which suggests that the microsphere containing retinoic acid according to the present invention remarkably and effectively inhibits the tumour cell growth.

Industrial Applicability

Since cytochrome P450 which metabolizes retinoic acid is induced even by a small amount of retinoic acid, repetitive administration of retinoic acid induces a problem that retinoic acid is rapidly decomposed into polar metabolite and thus, effective blood level cannot be maintained. This problem can be solved by a controlled drug release system for retinoic acid according to the present invention which slowly and continuously release retinoic acid over 5 weeks. Especially, in the microsphere containing each 4 wt % of DiPLE and retinoic acid, the drug release curve showed the release pattern similar to zero order drug release which reveals a nearly constant mode in drug release rate. This novel drug release system can minimize resistance induction by the oral retinoic acid administration, and possible to control the dissolution of microsphere and retinoic acid. Therefore, this system can effectively be used on or treatment of leukemia and various other cancers.

What is claimed is:

1. A controlled drug release system for retinoic acid characterized in that retinoic acid is incorporated into a microsphere prepared by mixing a biodegradable polymer, which is selected from the group consisting of poly-L-lactic acid, poly-D,L-lactic acid and poly(lactic-co-glycolic acid), and an amphiphilic AB type di-block copolymer, which is poly-L-lactic acid-polyethyleneglycol or poly(lactic acid-co-glycolic acid)-polyethyleneglycol, together, wherein the retinoic acid is selected from the group consisting of all-trans-retinoic acid, 13-cis-retinoic acid, 9-cis-retinoic acid, other retinoids and the mixture thereof, and the mixing ratio of the biodegradable polymer and the amphiphilic block copolymer is 1–20% by weight.

2. The drug release system for retinoic acid according to claim 1, wherein the mixing ratio of retinoic acid and microsphere is between 0.1~50 wt % based on the weight of microsphere.

3. The drug release system for retinoic acid according to claim 1, wherein the particle size of the microsphere is between 0.001 and 1000 μm.

4. The drug release system for retinoic acid according to claim 1, wherein the amphiphilic block copolymer comprises 1~20 wt % of poly-L-lactic acid-polyethyleneglycol di-block copolymer based on the total weight of the release system.

5. A pharmaceutical composition for the prevention or treatment of diseases selected from the group consisting of head and neck cancer, skin cancer, lung cancer, breast cancer, cervical cancer, bladder cancer, and acute promyelocytic leukemia comprising an effective amount of the drug release system according to claim 1, 2, 3, or 4 as an active ingredient and a pharmaceutically acceptable carrier.

* * * * *